United States Patent
Yagi

(10) Patent No.: US 11,877,795 B2
(45) Date of Patent: Jan. 23, 2024

(54) BALLOON CATHETER

(71) Applicant: Toray Industries, Inc., Tokyo (JP)

(72) Inventor: Takahiro Yagi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 241 days.

(21) Appl. No.: 16/967,845

(22) PCT Filed: Feb. 8, 2019

(86) PCT No.: PCT/JP2019/004537
§ 371 (c)(1),
(2) Date: Aug. 6, 2020

(87) PCT Pub. No.: WO2019/156195
PCT Pub. Date: Aug. 15, 2019

(65) Prior Publication Data
US 2021/0045806 A1 Feb. 18, 2021

(30) Foreign Application Priority Data

Feb. 9, 2018 (JP) ................................. 2018-021634

(51) Int. Cl.
*A61B 18/14* (2006.01)
*A61B 18/00* (2006.01)
(Continued)

(52) U.S. Cl.
CPC .. *A61B 18/1492* (2013.01); *A61B 2018/0022* (2013.01); *A61B 2018/00059* (2013.01);
(Continued)

(58) Field of Classification Search
CPC ........ A61B 18/1492; A61B 2018/0022; A61B 2018/00577; A61M 25/1025;
(Continued)

(56) References Cited

U.S. PATENT DOCUMENTS 4,955,895 A * 9/1990 Sugiyama ........... A61M 25/104
604/103.1
5,100,386 A 3/1992 Inoue
(Continued)

FOREIGN PATENT DOCUMENTS

JP 4-31714 5/1990
JP 3846508 11/2006
(Continued)

OTHER PUBLICATIONS

Overview of materials for Polyimide https://www.matweb.com/search/DataSheet.aspx?MatGUID=ab35b368ab9c40848f545c35bdf1a672&ckck=1 (Year: 2022).*
(Continued)

*Primary Examiner* — Jaymi E Della
*Assistant Examiner* — Abigail M Ziegler
(74) *Attorney, Agent, or Firm* — DLA Piper LLP (US)

(57) ABSTRACT

A balloon catheter includes a flexible outer cylinder shaft, a holding member connected to a proximal end portion of the outer cylinder shaft, a sealing member that maintains liquid tightness incorporated in the holding member, a flexible inner cylinder shaft, a tube having a Rockwell hardness of R 115 or more, a flexural modulus of 3.0 to 4.5 GPa, and a thickness of 0.06 to 0.12 mm, a push-in member connected to a proximal end portion of the inner cylinder shaft, a pull-out prevention member connected to the push-in member, and a balloon composed of an elastic material and connected to each of the distal end portion of the outer cylinder shaft and the proximal end portion of the inner cylinder shaft, wherein the tube is inserted over the inner cylinder shaft over an area thereof except for a connecting portion between the balloon and the inner cylinder shaft.

5 Claims, 1 Drawing Sheet

(51) Int. Cl.
*A61M 25/10* (2013.01)
*A61M 25/01* (2006.01)

(52) U.S. Cl.
CPC ............... *A61B 2018/00577* (2013.01); *A61B 2018/00791* (2013.01); *A61B 2018/00821* (2013.01); *A61M 25/1006* (2013.01); *A61M 2025/0175* (2013.01)

(58) Field of Classification Search
CPC .. A61M 2025/0004; A61M 2025/0175; A61M 2025/1068
See application file for complete search history.

(56) References Cited

U.S. PATENT DOCUMENTS

| | | | | |
|---|---|---|---|---|
| 5,176,698 | A * | 1/1993 | Burns | A61M 25/104 606/192 |
| 5,833,672 | A | 11/1998 | Kawata et al. | |
| 5,968,068 | A * | 10/1999 | Dehdashtian | A61F 2/958 604/164.08 |
| 7,695,465 | B2 * | 4/2010 | Tomaschko | A61M 25/104 604/524 |
| 2005/0154414 | A1 * | 7/2005 | Perreault | A61M 25/1006 606/192 |
| 2012/0059368 | A1 | 3/2012 | Takaoka et al. | |
| 2014/0114306 | A1 * | 4/2014 | Harada | A61B 18/1492 606/41 |
| 2015/0105815 | A1 | 4/2015 | Horn et al. | |
| 2016/0263355 | A1 * | 9/2016 | Katsurada | A61M 25/0102 |
| 2017/0000977 | A1 | 1/2017 | Storbeck et al. | |

FOREIGN PATENT DOCUMENTS

| | | |
|---|---|---|
| JP | 4062935 | 3/2008 |
| JP | 4191517 | 12/2008 |
| JP | 2009-247727 | 10/2009 |
| JP | 2016-533218 | 10/2016 |

OTHER PUBLICATIONS

Overview of materials for Nylon 6, Extruded https://www.matweb.com/search/DataSheet.aspx?MatGUID=726845c457b94b7cafe31d2e65739e1d (Year: 2022).*
Canadian Examination Report dated Aug. 11, 2021 from counterpart Canadian Application No. 3,087,084.

* cited by examiner

BALLOON CATHETER

TECHNICAL FIELD

This disclosure relates to a balloon catheter.

BACKGROUND

Balloon catheters are used in the medical field for performing minimally invasive treatments, and are used for a wide variety of treatments such as treatment of angiostenosis, cardiac valvular stenosis and cardiac arrhythmias as well as removal of embolic substances. A balloon catheter generally has a structure including; an outer cylinder shaft and an inner cylinder shaft that constitute the shaft of the balloon catheter; and a balloon. The balloon is formed by connecting the proximal end side of the balloon with the distal end portion of the outer cylinder shaft, and connecting the proximal end side of the balloon with the distal end portion of the inner cylinder shaft. When a balloon catheter has the above described structure, the balloon is inflated by allowing a fluid to flow into a flow path between the outer cylinder shaft and the inner cylinder shaft.

In general, low resistance during insertion of a catheter into the body of a patient is more preferred. However, in a balloon catheter, resistance during insertion is increased since the balloon portion of the balloon catheter has a high volume. To reduce the volume of the balloon portion, methods are known in which the balloon portion is kept folded during insertion.

However, when a balloon is formed using a flexible material such as a natural rubber, a synthetic rubber, a polyurethane or silicon, it is difficult to keep the balloon folded, because of its flexibility. To solve such a problem, a balloon catheter has been reported in which a wire material made of a material that is less easily stretched compared to an outer tube is fixed to the outer tube, and a hard core material is inserted removably into an inner tube so that the outer tube and the inner tube are slidable relative to each other while integrating the entire structure (JP 4-31714 B). That wire material made of a material that is less easily stretched compared to the outer tube enables to push-in the inner tube while reducing the stretching of the outer tube, as a result of which the balloon can be securely stretched in the longitudinal direction.

Likewise, an ablation catheter with a high frequency balloon is reported that utilizes a technique of securely stretching a balloon while using a balloon made of a flexible material. That ablation catheter is configured such that the balloon is stretchable in a state where a guide wire is inserted into the inner cylinder shaft, instead of using a hard core material, whereby the balloon can be securely stretched in the longitudinal direction (JP 4062935 B).

Also reported is a catheter in which, to prevent buckling of the inner cylinder shaft of the catheter, a double-layered tube composed of a tube made of a hard material and a tube made of a soft material is used as the inner cylinder shaft to adjust flexural rigidity. Further, in that catheter, the inner cylinder shaft and the outer cylinder shaft are connected to prevent buckling of a guide wire (JP 3846508 B).

As a balloon catheter employing another method, a balloon catheter is also reported in which the volume of the balloon portion can be reduced even if the balloon is caught by an introducer during withdrawal of the catheter to cause wrinkles of the balloon, because the distal end portion of the balloon is configured to be movable (JP 4191517 B).

However, in the balloon catheter disclosed in JP 4-31714 B, the hard core material needs to be removably inserted inside the inner tube. This results in an increase in the time and work for carrying out the operation. Further, when it is desired to maintain the stretching of the balloon even at a curvature in a blood vessel, for example, the catheter operation needs to be carried out with the hard core material being inserted inside the inner tube. As a result, there are possibilities that the balloon catheter may fail to conform to the curvature of the blood vessel.

In the ablation catheter with a high frequency balloon disclosed in JP 4062935 B, when the balloon is stretched, the restoring force of the balloon to restore its original shape applies a compressive load on the inner cylinder shaft. This leads to the problem that the guide wire or the inner cylinder shaft is buckled. In an ablation catheter with a high frequency balloon, in particular, the balloon is heated during the operation, and thus it causes deformation of the balloon or softening of the inner cylinder shaft due to heat. As a result, an increase in the volume of the balloon or buckling of the inner cylinder shaft are more likely to occur compared to the initial state.

In the balloon catheter disclosed in JP 3846508 B, the inner cylinder shaft is connected with the outer cylinder shaft, and thus the shafts are not slidable relative to each other. Further, since the inner cylinder shaft is not easily stretched due to containing a hard material, the balloon portion of the catheter is more likely to get caught by the distal end portion of the introducer sheath when the balloon catheter is withdrawn from the body of a patient during a catheter operation. An attempt to withdraw the catheter in this state, as it is, causes the volume of the balloon to shift and accumulate to the distal end portion, resulting in problems such as a failure to withdraw the balloon catheter from the introducer, and a difficulty to withdraw the balloon catheter, possibly damaging the blood vessel of the patient. When inflating a highly flexible balloon, a tensile load is applied in the longitudinal direction of the inner cylinder shaft, to cause a stretching effect on the inner cylinder shaft. When the inner cylinder shaft is made of a hard material, the stretching effect within the elastic range of the shaft fails to work, and a load due to the inflation of the balloon is accumulated to the connecting portion of the balloon with the inner cylinder shaft. This may possibly lead to the occurrence of damage in the connecting portion, or the stretching of the inner cylinder shaft to cause a decrease in the inner diameter, thereby impairing slidability with the guide wire.

When the balloon in the balloon catheter disclosed in JP 4191517 B is inflated, the balloon inflates not only to cause an increase in the outer diameter thereof, but also to extend in the longitudinal direction of the balloon catheter. Therefore, the fluid volume required to inflate the balloon to achieve a desired inflated diameter will be increased compared to a usual device. Further, when the balloon catheter is configured such that it can be used in combination with a guide wire, the inner cylinder shaft needs to have at least two lumens. This causes an increase in the outer diameter of the inner cylinder shaft, and a decrease in the clearance between the outer diameter of the inner cylinder shaft and the inner diameter of the outer cylinder shaft, as a result of which the area of the flow path of the balloon lumen is decreased. An increase in the fluid volume in the balloon and a decrease in the area of the flow path of the balloon lumen result in the problem of decelerating the inflation and deflation speed of the balloon. As a result, in treating cardiac valvular stenosis, for example, there is a possibility that the blood flow needs to be blocked for a longer period of time.

Due to the above mentioned circumstances, a means for solving a number of problems associated with a balloon catheter including a balloon made of a flexible material, all at once, have not yet been disclosed.

Therefore, it could be helpful to provide a balloon catheter in which the volume of the balloon upon deflation can be reduced without decelerating the speed of inflation and deflation of the balloon.

SUMMARY

I thus provide:
(1) A balloon catheter, including:
   an outer cylinder shaft having flexibility;
   a holding member for an operator to hold during operation, the holding member being connected to the proximal end portion of the outer cylinder shaft;
   a sealing member which maintains liquid tightness, the sealing member being incorporated in the holding member;
   an inner cylinder shaft having flexibility;
   a tube having a Rockwell hardness of R 115 or more, a flexural modulus of from 3.0 to 4.5 GPa, and a thickness of from 0.06 to 0.12 mm;
   a push-in member connected to the proximal end portion of the inner cylinder shaft;
   a pull-out prevention member connected to the push-in member; and
   a balloon composed of an elastic material and connected to each of the distal end portion of the outer cylinder shaft and the distal end portion of the inner cylinder shaft;
   wherein the tube is inserted over the inner cylinder shaft over the area thereof except for the connecting portion between the balloon and the inner cylinder shaft.
(2) The balloon catheter according to (1), wherein the clearance between the inner diameter of the tube and the outer diameter of the inner cylinder shaft is from 0.01 to 0.1 mm.
(3) The balloon catheter according to (1) or (2), wherein the inner cylinder shaft has a tensile elastic modulus of from 500 to 1,400 MPa, a thickness of from 0.1 to 0.23 mm and a yielding strength of 25 MPa or more.
(4) The balloon catheter according to any one of (1) to (3), wherein the tube and the inner cylinder shaft are fixed with each other only at the proximal end portion of the tube and the proximal end portion of the inner cylinder shaft.
(5) The balloon catheter according to any one of (1) to (3), wherein the tube and the inner cylinder shaft are fixed with each other only at the distal end portion of the tube and the distal end portion of the inner cylinder shaft.
(6) The balloon catheter according to any one of (1) to (5), wherein the push-in member has a shape of a pipe with varying outer diameter;
   wherein the transition portion where the outer diameter is varying, of the push-in member has a tapered shape, and the respective outer diameters of the pipe are configured to decrease in the direction from the proximal end side toward the distal end side of the pipe; and
   wherein the pull-out prevention member is provided on the pipe portion of the push-in member at a position where the first change in the outer diameter occurs in the direction toward the distal end side, in a state where the balloon is at its equilibrium length.
(7) A balloon catheter for ablation, including:
   the balloon catheter according to any one of (1) to (6);
   an electrode lead wire capable of conducting a high frequency current and provided in the space between the inner cylinder shaft and the outer cylinder shaft and;
   a temperature sensor lead wire for transmitting the temperature in the balloon to the outside, the temperature sensor lead wire being provided between the space between the inner cylinder shaft and the outer cylinder shaft; and
   a lead wire cladding tube through which the electrode lead wire and the temperature sensor lead wire are inserted so that the electrode lead wire and the temperature sensor lead wire are led into the space between the inner cylinder shaft and the outer cylinder shaft, from the outside;
   wherein the electrode lead wire and the temperature sensor lead wire are made of metals different from each other, and are in contact with each other in the interior of the balloon; and
   wherein the lead wire cladding tube is in the form of a pipe including a portion with varying outer diameter, and is provided on the distal side from the handle portion of the push-in member to be slidable while maintaining liquid tightness via the sealing member.

When a tube having a Rockwell hardness of R 115 or more, a flexural modulus of from 3.0 to 4.5 GPa, and a thickness of from 0.06 to 0.12 mm is inserted over the inner cylinder shaft over the area thereof except for the connecting portion between the balloon and the inner cylinder shaft, it is possible to improve the buckling resistance strength of the shaft portion of the catheter against the restoring force of the balloon, which force is generated due to extending the stretch distance of the balloon during the insertion of the catheter into the body without impairing the trackability of the shaft portion to the curvature of a blood vessel.

Figure 1:
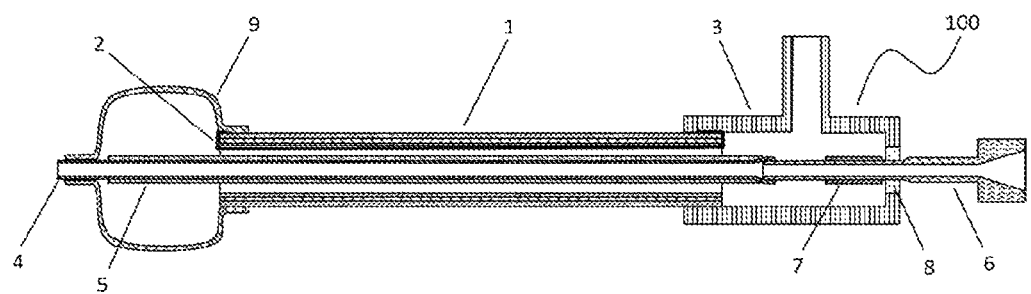
FIG. 1 is a schematic side view in the longitudinal direction of a balloon catheter according to an example.

REFERENCE SIGNS LIST 1 outer cylinder shaft
2 stretch prevention member
3 holding member
4 inner cylinder shaft
5 tube
6 push-in member
7 pull-out prevention member
8 sealing member
9 balloon
10 coil portion of electrode lead wire
11 electrode lead wire
12 temperature sensor lead wire
13 lead wire cladding tube
14 filler
100 balloon catheter
200 balloon catheter

DETAILED DESCRIPTION

My balloon catheter is characterized by including:
an outer cylinder shaft having flexibility;
a holding member for an operator to hold during operation, the holding member being connected to the proximal end portion of the outer cylinder shaft;
a sealing member which maintains liquid tightness, the sealing member being incorporated in the holding member;
an inner cylinder shaft having flexibility;
a tube having a Rockwell hardness of R 115 or more, a flexural modulus of from 3.0 to 4.5 GPa, and a thickness of from 0.06 to 0.12 mm;
a push-in member connected to the proximal end portion of the inner cylinder shaft;
a pull-out prevention member connected to the push-in member; and
a balloon composed of an elastic material and connected to each of the distal end portion of the outer cylinder shaft and the distal end portion of the inner cylinder shaft;
wherein the tube is inserted over the inner cylinder shaft over the area thereof except for the connecting portion between the balloon and the inner cylinder shaft.

Preferred examples will now be described in detail, with reference to the drawings. However, this disclosure is in no way limited by the examples. The same elements are denoted by the same reference numerals, and redundant description will be omitted. Further, the dimensional ratios in the drawings do not always coincide with those in the description.

The expression "distal end side of the balloon catheter" as used herein refers to the side of the balloon in the longitudinal direction of the balloon catheter. Further, the expression "proximal end side of the balloon catheter" as used herein refers to the side of the holding member in the longitudinal direction of the balloon catheter.

The term "monolayer tube" refers to a tube whose cross sectional shape has a single layer structure; and the term "multilayer tube" refers to a tube formed from a combination of a plurality of materials, and whose cross sectional shape has a multilayer structure composed of a plurality of layers.

The term "equilibrium length" of a balloon refers to the length of the balloon in the longitudinal direction, when a load due to deformation of the balloon is not generated at the connecting portions of the balloon, and to the length of the balloon from the connecting portion between the distal end side of the balloon and the inner cylinder shaft, to the connecting portion between the proximal end side of the balloon and the outer cylinder shaft.

FIG. 1 is a schematic side view in the longitudinal direction of the balloon catheter according to an example. A balloon catheter 100 shown in FIG. 1 includes an outer cylinder shaft assembly, an inner cylinder shaft assembly and a balloon 9.

In the balloon catheter 100, the outer cylinder shaft assembly includes an outer cylinder shaft 1, a stretch prevention member 2, a holding member 3 and a sealing member 8.

The outer cylinder shaft 1 may have either a structure of a monolayer tube or a structure of a multilayer tube. When the outer cylinder shaft 1 has a structure of a multilayer tube, for example, the outer cylinder shaft 1 may be a multilayer tube composed of three layers, which are an outer layer, an intermediate layer and an inner layer.

When the outer cylinder shaft 1 is a multilayer tube composed of three layers, the material of the outer layer is preferably a flexible polymeric material having an excellent antithrombotic property. Examples thereof include vinyl chloride, polyurethanes, polyamides, polyether block amide copolymers, polypropylene, polyolefins and polyethylene terephthalate. To allow the welding by heat of the outer layer to the balloon 9 to be described later, the material of the outer layer is preferably a polyurethane or a polyether block amide copolymer, which is compatible with the material of the balloon 9. The material of the intermediate layer may be any material as long as it is a flat wire made of a metal, and may be, for example, one made of stainless steel, which is usually used in a medical device. The material of the inner layer may be, for example, but not limited to, a fluorine-based polymer such as PTFE to improve the slipperiness of the inner surface of the lumen and the stretch resistance as a tube, of the outer cylinder shaft 1.

The stretch prevention member 2 is a member that prevents the outer cylinder shaft 1 from being stretched due to the restoring force of the balloon 9 to restore its equilibrium length, when the balloon catheter 100 is inserted into a blood vessel in a state where the balloon 9 being deformed. To achieve this, the stretch prevention member 2 is made of a material having a higher tensile strength than the restoring force of the balloon 9. Further, the stretch prevention member 2 may have any shape as long as the stretching of the outer cylinder shaft 1 can be prevented. The stretch prevention member 2 may be, for example, in the shape of a monofilament, a multifilament or a strip that is attached or pasted on the inner surface of the outer cylinder shaft 1 over the entire length thereof in the longitudinal direction.

Further, in the balloon catheter 100, the length of the stretch prevention member 2 in the form of a monofilament in the longitudinal direction is longer than the length of the outer cylinder shaft 1 in the longitudinal direction. By this arrangement, the respective ends of the stretch prevention member 2 are configured to protrude from both ends, at the opening on the distal end side and the opening on the proximal end side, of the lumen of the outer cylinder shaft 1, during the production process. The protruded portions are configured to be folded toward the external surface of the outer cylinder shaft 1. Further, at the opening on the proximal end side of the outer cylinder shaft 1, the sealing member 8 that allows the inner cylinder shaft 4 and the outer cylinder shaft 1 to slide relative to each other while maintaining the liquid tightness is provided, and the holding member 3 for an operator to hold during the operation is attached to surround the outer periphery of the outer cylinder shaft 1.

The material of the stretch prevention member 2 is suitably a material which does not interfere with the ability of the balloon catheter to conform to the curvature of a blood vessel or the like, and which has a high tensile strength. The material is preferably an aramid fiber or a polyacrylate fiber.

The holding member 3 is a member for an operator to hold during the operation, and may have any shape as long it is an ergonomically suitable shape which allows the operator to easily carry out the operation. The holding member 3 may be, for example, in the shape of "Y", but not particularly limited thereto. The holding member 3 is attached to the proximal end side of the outer cylinder shaft 1 to surround the outer periphery thereof.

The material of the holding member 3 is preferably a plastic having a certain hardness, from the viewpoint of ensuring the ease of molding and the strength. The material thereof may be, for example, a plastic such as a styrene polymer, an acrylic polymer, polypropylene, polyethylene, a fluorine polymer or polyacetal.

The inner cylinder shaft 4 is a member whose inner surface constitutes the lumen for a guide wire for the balloon catheter 100, and which forms an inflation lumen for the balloon 9 by being inserted into the lumen of the outer cylinder shaft 1.

The inner cylinder shaft 4 is preferably composed of a material having a tensile elastic modulus of 500 to 1,400 MPa and a yielding strength of 25 MPa or more, when measured by the test method in accordance with ISO 527, and having a thickness of 0.1 to 0.23 mm. Specific examples of the material include polyamides and polyether block amides, but not limited thereto.

The tube 5 is a member for preventing the kinking or buckling of the inner cylinder shaft 4 due to the restoring force of the balloon 9, which occurs when the balloon 9 is stretched for the purpose of reducing the volume of the balloon 9 to insert the balloon catheter 100 into a blood vessel. Since the tube 5 is inserted over the inner cylinder shaft over almost the entire length of the inner cylinder shaft 4 except for a part at the distal end portion of the inner cylinder shaft 4, the inner cylinder shaft 4 and the tube 5 are slidable relative to each other. This provides a mechanism in which the tensile force applied to the inner cylinder shaft 4 during the inflation of the balloon causes a stretching effect only on the inner cylinder shaft. The above described relationship between the inner cylinder shaft 4 and the tube 5 enables to achieve both the buckling resistance during the stretching of the balloon and the flexibility during the inflation of the balloon.

The tube 5 is only required to be inserted over the inner cylinder shaft 4. However, the inner cylinder shaft assembly is preferably formed by fixing the inner cylinder shaft 4 and the tube 5 only at either the end portion on the distal end side of the tube 5 or the end portion on the proximal end side of the tube 5. As described above, when the inner cylinder shaft 4 and the tube 5 are fixed only at the proximal end portion of the tube 5 and the proximal end portion of the inner cylinder shaft 4, or only at the distal end portion of the tube 5 and the distal end portion of the inner cylinder shaft 4, it is possible to maintain the mechanism in which the stretching effect occurs only on the inner cylinder shaft 4, while preventing the interference between members such as, for example, one member running on another member, with a minimum number of fixing sites.

Examples of the material of the tube 5 include polyimides, polyether ether ketones, polyphenylene sulfides, polyetherimides and polyamideimides, but not limited thereto.

The push-in member 6 is a member that allows an operator to carry out the operation of stretching the balloon 9 to insert the balloon catheter 100 into a blood vessel. The push-in member 6 includes a pipe portion having two or more outer diameters at the portion other than the holding portion of the push-in member 6. The respective outer diameters of the pipe portion are configured to increase in the direction from the distal end side toward the proximal end side thereof, and the transition portion where the outer diameter is varying has a tapered shape. Further, the end portion on the distal end side of the push-in member 6 is connected to the end portion on the proximal end side of the inner cylinder shaft 4.

It is preferred to use a hard polymer or a metallic material as the material of the pipe portion of the push-in member 6 so that an operator can easily carry out the pushing operation. To employ a metallic material is preferred. The metallic material is preferably stainless steel. The push-in member 6 preferably includes a handle portion at the end portion on the proximal end side thereof so that the operator can easily hold the push-in member 6. The material of the handle portion is preferably a hard polymer or a metallic material. The surface of the handle portion is preferably roughened by being subjected to knurling or sand blasting, from the viewpoint of preventing slippage.

Although it varies depending on the tightening force of the sealing member 8, when the pipe portion on the proximal end side of the push-in member 6 is configured to include a step of from 0.3 to 0.4 mm and to have a length of the tapered transition portion of from 0.5 to 1 mm, the operator can feel the step by touch when sliding the inner cylinder shaft assembly relative to the outer cylinder shaft assembly. At the same time, the load generated when the sealing member 8 to be described later passes over the step in the pipe portion of the push-in member 6 is controlled within 10 to 15N and, thus, the operator can carry out the operation to pass over the step without feeling stress.

The pull-out prevention member 7 is a member which is in the form of a cylinder having a thickness of 0.1 to 0.4 mm, which is connected to the pipe portion of the push-in member 6 having the second largest outer diameter, and provided to prevent the balloon 9 of the balloon catheter 100 from becoming shorter than its equilibrium length, toward the proximal end side.

The material of the pull-out prevention member 7 is preferably a hard polymer or a metal. In attaching the pull-out prevention member 7 to the push-in member 6, an attachment method such as adhesion using an adhesive, welding or the like may be selected to suit the material of the pull-out prevention member 7.

In the balloon catheter 100, the balloon 9 is formed from an elastic material. Specific examples of the elastic material for forming the balloon 9 include silicon, polyether block amide copolymers, polyurethanes, natural rubbers and synthetic rubbers. The balloon 9 may also have a multilayer structure. In using a balloon having a multilayer structure, the balloon may be obtained, for example, by adhering a mesh formed by weaving false twist yarns composed of a polyurethane or a polyester in the form of a tube, to a natural rubber, using a rubber cement. The hardness of the balloon 9 may vary depending on the subject to be treated. In using the balloon 9 made of a single material in atrial fibrillation ablation, the material preferably has a Shore A hardness of 100 or less.

The sealing member 8 enables the inner cylinder shaft assembly, to be described later, to slide relative to the outer cylinder shaft assembly, while keeping the interior of the balloon catheter 100 in a liquid tight state by closing the opening of the holding member 3.

The material of the sealing member 8 is preferably a soft material, from the viewpoint of allowing the inner cylinder shaft assembly to be slidable while keeping liquid tightness. For example, a silicone rubber, a synthetic rubber, or a styrene-based thermoplastic elastomer is preferred.

For example, a slit valve obtained by forming a slit at a part of a sheet made of a soft material may be used as the sealing member 8 to be incorporated into the holding member 3. Alternatively, after providing a cap-fitting structure to the holding member 3, an O-ring or a cylindrical soft material may be used as the sealing member 8, such that the sealing member 8 is tightened utilizing the cap-fitting structure.

Further, in the balloon catheter 100, the inner cylinder shaft assembly is composed of the inner cylinder shaft 4, the tube 5, the push-in member 6, the pull-out prevention member 7 and the sealing member 8.

When the elastic material forming the balloon 9 is a poorly weldable material such as a natural rubber or a synthetic rubber, it is usually difficult to attach the balloon 9 to the outer cylinder shaft 1. In this example, a short pipe made of a hard polymer or a metal may be inserted into the distal end portion of the outer cylinder shaft 1 to protrude from the distal end portion of the outer cylinder shaft 1, and the poorly weldable material may be adhered to the protruded portion of the pipe, by winding a thread such as a nylon string therearound.

In the same manner, when the elastic material forming the balloon 9 is a poorly weldable material such as a natural rubber or a synthetic rubber, it is usually difficult to attach the balloon 9 to the inner cylinder shaft 4. In this example, a short pipe made of a hard polymer or a metal may be inserted into the distal end portion of the inner cylinder shaft 4, and the poorly weldable material may be adhered to the portion of the outer periphery of the inner cylinder shaft 4 at which the pipe is present, by winding a thread such as a nylon string therearound.

The equilibrium length of the balloon 9 may be set as appropriate depending on the subject to be treated. In either of treating cardiac valvular stenosis or atrial fibrillation, the balloon 9 preferably has an equilibrium length of 20 to 30 mm. The length of the outer cylinder shaft 1 may also be set as appropriate depending on the subject to be treated. The outer cylinder shaft 1 preferably has a length of 200 to 1,100 mm when used to treat cardiac valvular stenosis, and preferably 700 to 1,000 mm when used to treat atrial fibrillation.

The outer diameter of the balloon 9 upon inflation may be set as appropriate depending on the subject to be treated. The balloon 9 preferably has an outer diameter upon inflation of 13 to 30 mm when used to treat cardiac valvular stenosis, and preferably 20 to 35 mm when used to treat atrial fibrillation.

The balloon catheter 100 is formed by inserting the above described inner cylinder shaft assembly into the outer cylinder shaft assembly, and adhering the end portions on the distal end side of the inner cylinder shaft assembly and the outer cylinder shaft assembly with the balloon 9.

During formation of the balloon catheter 100, the inner cylinder shaft assembly is inserted into the outer cylinder shaft assembly such that the position of the sealing member 8 in the outer cylinder shaft assembly is adjusted to coincide with the position of the end portion on the proximal end side of the small diameter portion of the push-in member 6 in the inner cylinder shaft assembly. In this state, the pull-out prevention member 7 is attached onto the small diameter portion of the push-in member 6, at a position where the sealing member 8 is not provided, and the balloon 9 is attached to the end portion on the distal end side of the outer cylinder shaft 1 and the end portion on the distal end side of the inner cylinder shaft 4 (at the portion thereof over which the tube 5 is not inserted), to form the balloon catheter 100 in which the balloon 9 is at its equilibrium length.

When forming the balloon catheter 100, the pipe portion of the push-in member 6 is preferably inserted until it reaches the lumen of the outer cylinder shaft 1 to further enhance the rigidity of the tube portion of the inner cylinder shaft assembly. In this example, the length of the balloon catheter may be set as appropriate depending on the subject to be treated. The balloon catheter preferably has a length of 600 to 900 mm in approaching from the femoral artery to the heart valves, and preferably 500 to 800 mm in approaching from the femoral vein to the left atrium.

Further, when the pipe portion of the push-in member 6 is inserted until it reaches the outer cylinder shaft 1, the lengths of the inner cylinder shaft 4 and the tube 5 are also adjusted as appropriate corresponding to the length of the balloon catheter. The inner cylinder shaft 4 preferably has a length of 200 to 400 mm in approaching from the femoral artery to the heart valves, and preferably 100 to 300 mm in approaching from the femoral vein to the left atrium.

Figure 2:
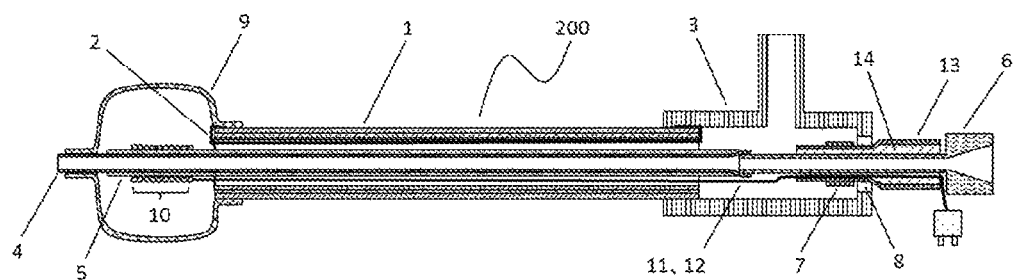
FIG. 2 is a schematic side view in the longitudinal direction of a balloon catheter according to another example.

Next, another example of the balloon catheter will be described. FIG. 2 is schematic side view in the longitudinal direction of a balloon catheter 200. The outer cylinder shaft assembly included in the balloon catheter 200 has the same structure as that of the outer cylinder shaft assembly included in the balloon catheter 100. However, the inner cylinder shaft assembly included in the balloon catheter 200 has a structure different from the structure of the outer cylinder shaft assembly included in the balloon catheter 100.

Specifically, in the inner cylinder shaft assembly included in the balloon catheter 200, the end portion on the proximal end side of the inner cylinder shaft 4 is attached to the end portion on the distal end side of the push-in member 6, the tube 5 made of polyimide is inserted over the inner cylinder shaft 4 over the entire length thereof except for a part at the distal end portion of the inner cylinder shaft 4, and the tube 5 is fixed only to the end portion on the proximal end side of the inner cylinder shaft 4.

The balloon catheter 200 is configured to use a high frequency current, and includes an electrode lead wire 11 and a temperature sensor lead wire 12. The electrode lead wire 11 and the temperature sensor lead wire 12 are each covered by an electrically insulating protective coating over almost the entire length thereof. The electrically insulating protective coating is provided except for the portion of each of the lead wires desired to be energized, thereby allowing for a high frequency energization and an electrical contact with the other lead wire. In addition, the electrode lead wire 11 and the temperature sensor lead wire 12 are provided on the inner cylinder shaft 4 over almost the entire lengths of the tube 5 and the push-in member 6.

Inside the balloon 9, the electrode lead wire 11 are wound in the form of a coil around the outer periphery of the tube 5, and fixed thereto. By this arrangement, it is preferred that a coil portion 10 of the electrode lead wire be formed on the distal end side of the electrode lead wire 11. Such a configuration enables to prevent the impairment of the trackability of the inner cylinder shaft 4 in the balloon portion to the curvature, and allows for a high frequency energization between the counter electrode plate to be pasted on the body surface of a patient and the electrode lead wire, in a more suitable manner.

Further, when the portion of the electrode lead wire 11 at which the electrically insulating protective coating is not provided comes into contact, inside the balloon 9, with the temperature sensor lead wire 12 at which the electrically insulating protective coating is not provided, the temperature sensor lead wire 12 being composed of another metal, the electrode lead wire 11 and the temperature sensor lead wire 12 are energized. Since the electrode lead wire 11 and the temperature sensor lead wire 12 are made of metals different from each other, a thermocouple (a temperature sensor utilizing a weak voltage (thermoelectromotive force) generated corresponding to the temperature difference between different metals) is formed at the contact point, at this time, thereby enabling to measure the temperature inside the balloon 9.

When a high frequency current is used as in the balloon catheter 200, the end portion on the distal end side of the outer cylinder shaft 1 is preferably configured such that the metal braid of the intermediate layer of the outer cylinder shaft 1 is not exposed to the high frequency current, for example, by attaching a monolayer tube to the distal end portion of the outer cylinder shaft 1 by welding so that the high frequency current can be prevented from flowing into the metal braid. Further, the outer layer of the outer cylinder shaft 1 preferably has a thickness larger than the thickness of the balloon 9.

However, in a balloon catheter using a high frequency current such as the balloon catheter 200, the pipe portion of the push-in member 6 is preferably kept in a cylindrical shape as it is, without providing a step thereto so that the electrode lead wire 11 and the temperature sensor lead wire 12 on the outer periphery of the pipe portion of the push-in member 6 can be arranged straight.

The material of an electrode 10 for high frequency energization is preferably, for example, copper, silver, gold, platinum or tungsten, or an alloy thereof. In the balloon catheter 200, the distal end portion of the electrode lead wire 11 forms the coil portion 10 of the electrode lead wire. By not providing the electrically insulating protective coating at the coil portion 10 of the electrode lead wire, the coil portion 10 of the electrode lead wire is made capable of high frequency energization. In this example, the electrode lead wire 11 is preferably in the form of a coil, because it facilitates the high frequency energization.

The electrode lead wire 11 is a member for conducting a high frequency current inside the balloon of an ablation balloon catheter using a high frequency power supply.

The material of the electrode lead wire 11 may be, for example, copper, silver, gold, platinum or tungsten, or an alloy thereof. From the viewpoint of preventing the occurrence of a short circuit, an electrically insulating protective coating such as a fluorine polymer coating, is provided on the surface of the electrode lead wire 11. The electrode lead wire 11 preferably has a diameter of 0.05 to 0.4 mm from a practical point of view, but not particularly limited thereto.

The temperature sensor lead wire 12 and the electrode lead wire 11 are members made of metals different from each other that are in contact with each other in the interior of the balloon 9 to form a thermocouple to measure the temperature inside the balloon 9, and transmit the temperature inside the balloon 9 as a voltage to the outside.

To form a thermocouple, the temperature sensor lead wire 12 is formed using, as a material, a metal different from the metal used for forming the electrode lead wire 11. The temperature sensor lead wire 12 may be formed using any metal as long as it is different from the metal used for forming the electrode lead wire 11. The material of the temperature sensor lead wire 12 is preferably, for example, nickel, chromium or platinum, or an alloy thereof. From the viewpoint of preventing the occurrence of a short circuit, an electrically insulating protective coating such as a fluorine polymer coating, is preferably provided on the surface of the temperature sensor lead wire 12. The temperature sensor lead wire 12 preferably has a diameter of 0.05 to 0.4 mm from a practical point of view, but not particularly limited thereto.

A lead wire cladding tube 13 is a cladding tube provided on the outer periphery of the push-in member 6, and through which the electrode lead wire 11 and the temperature sensor lead wire 12 are inserted. In the balloon catheter 200, the electrode lead wire 11 and the temperature sensor lead wire 12 connected to an external power supply are inserted through the lead wire cladding tube 13, and the electrode lead wire 11 and the temperature sensor lead wire 12 are led from the outside into the space between the inner cylinder shaft 4 and the outer cylinder shaft 1, through the lead wire cladding tube 13. Further, the lead wire cladding tube 13 is provided on the distal end side from the handle portion of the push-in member 6 in the longitudinal direction to be slidable relative to the sealing member 8 while maintaining liquid tightness therewith.

Further, in the balloon catheter 200, the lead wire cladding tube 13 is in the form of a pipe with varying outer diameter, and includes a small diameter portion, an intermediate portion and a large diameter portion from the proximal end side in the longitudinal direction, in the order mentioned. Since the intermediate portion has a tapered shape, the lead wire cladding tube 13 has a step as a whole.

Although it varies depending on tightening force of the sealing member 8, as with the balloon catheter 100, it is preferred that the lead wire cladding tube 13 be configured to include a step of 0.3 to 0.4 mm, and to have a length of the tapered transition portion of 0.5 to 1 mm, when the sliding force between the outer cylinder shaft assembly and the inner cylinder shaft assembly at the pipe portion on the proximal end side is 10 to 15N, since, by this arrangement, the operator can feel the step by touch, and carry out the operation to pass over the step without feeling stress.

The lead wire cladding tube 13 is preferably made of a hard material so that the operator can easily carry out a push-in operation. Specifically, the material of the lead wire cladding tube may be, for example, a hard polymer or a metallic material. However, the use of a metallic material as the material is preferred, and the use of a stainless steel as the material is more preferred because of its high corrosion resistance.

Further, when attaching the pull-out prevention member 7 to the lead wire cladding tube 13, an attachment method such as adhesion using an adhesive, welding or the like may be selected to suit the material of the pull-out prevention member 7.

A filler 14 is a member that prevents liquid from infiltrating into the interior of the lead wire cladding tube 13. The electrode lead wire 11 and the temperature sensor lead wire 12 present on the outer periphery of the pipe of the push-in member 6 other than the holding portion thereof, are inserted through the interior of the lead wire cladding tube 13, and the filler 14 is filled into the gap between the lead wire cladding tube 13 and the outer periphery of the pipe of the push-in member 6 other than the holding portion thereof.

The material of the filler 14 may be, for example, but not limited to, an urethane-based or a silicon-based sealing material or an epoxy adhesive to integrate the push-in member 6 and the lead wire cladding tube 13 while filling the gap therebetween in a liquid tight manner.

The balloon catheter 200 is formed by inserting the above described inner cylinder shaft assembly into the outer cylinder shaft assembly, and adhering the end portions on the distal end side of the inner cylinder shaft assembly and the outer cylinder shaft assembly with the balloon 9.

At this time, the inner cylinder shaft assembly is inserted into the outer cylinder shaft assembly such that the position of the sealing member 8 in the outer cylinder shaft assembly is disposed to coincide with the position of the end portion on the proximal end side of the small diameter portion of the lead wire cladding tube 13 in the inner cylinder shaft assembly. In this state, the pull-out prevention member 7 is attached onto the small diameter portion of the lead wire cladding tube 13, at a position where the sealing member 8 is not provided, and the balloon 9 is attached to the end portion on the distal end side of the outer cylinder shaft 1 and the end portion on the distal end side of the inner cylinder shaft 4 (at the portion thereof over which the tube 5 is not inserted), to form the balloon catheter 200 in which the balloon 9 is at its equilibrium length.

The electrode lead wire 11 and the temperature sensor lead wire 12 present on the outer periphery of the pipe of the push-in member 6 other than the holding portion thereof, are inserted through the interior of the lead wire cladding tube 13, and the filler 14 is filled into the gap between the lead wire cladding tube 13 and the outer periphery of the pipe of the push-in member 6 other than the holding portion thereof.

EXAMPLES

Specific examples of my balloon catheters will now be described with reference to FIG. 1.

Example 1

A tube having a three-layer structure was prepared with a polyether block amide copolymer as the material of the outer layer, a braid structure composed of stainless steel flat wires as the material of the intermediate layer, and PTFE as the material of the inner layer. To the distal end portion of the resulting tube having a three-layer structure, a monolayer tube (length: 4 mm) made of a polyether block amide copolymer was attached by heat welding, to prepare a braid tube. The thus obtained braid tube had an outer diameter of 3.1 mm, an inner diameter of 2.6 mm, and a length of 1,050 mm.

Next, a single-stepped pipe having a small diameter portion on the distal end side thereof and a small diameter portion on the proximal end side (the pipe is made of stainless steel and includes: a small diameter portion having an outer diameter of 2 mm, an inner diameter of 1.84 mm and a length of 7 mm; a large diameter portion having an outer diameter of 2.4 mm, an inner diameter of 2.24 mm and a length of 3 mm) was prepared. The end portion of an aramid fiber (having a length of 1,200 mm and a diameter of 0.3 mm) was wound around and fixed to the step portion of the stepped pipe. After allowing the aramid fiber to pass through the braid tube, the large diameter portion of the stepped pipe was fixed to the distal end portion of the braid tube with an adhesive, to prepare the outer cylinder shaft 1.

A Y-shaped connector having a cap-fitting structure to which an O-ring can be fitted was used as the holding member 3. As the stretch prevention member 2, the aramid fiber was provided to the lumen of the outer cylinder shaft 1 to extend over the entire length thereof. In a state where the aramid fiber was folded back on the outer periphery of the end portion on the proximal end side of the outer cylinder shaft 1, the end portion on the proximal end side of the outer cylinder shaft 1 and the tube connecting port of the Y-shaped connector were fixed to each other by an adhesive.

As the push-in member 6, a stainless steel pipe provided with a handle portion and having an outer diameter varying in three steps was prepared. When the portions of the push-in member 6 having different diameters are respectively defined as a large diameter portion, an intermediate portion and a small diameter portion, in the order from the proximal end side in the longitudinal direction, the large diameter portion had an outer diameter of 2.1 mm and a length of 60 mm; the intermediate portion had an outer diameter of 1.8 mm and a length of 10 mm; the taper length, which is the length of the transition portion from the large diameter portion to the intermediate portion, was 0.5 mm; and the small diameter portion had an outer diameter of 1.16 mm and a length of 805 mm. The push-in member 6 had a minimum inner diameter of 1.0 mm.

Subsequently, a screw-type cap for the holding member 3 as well as an O-ring having an inner diameter of 1.4 mm and a wire diameter of 1.5 mm were inserted over the push-in member 6 (such that the cap was disposed on the proximal end side). The O-ring was positioned at the end portion on the proximal end side of the intermediate portion, and the pull-out prevention member 7 was fixed with an adhesive on the intermediate portion of the push-in member 6, at a position on the distal end side from the O-ring. The pull-out prevention member 7 is made of polyimide, and had an inner diameter of 1.9 mm, a thickness of 0.06 mm and a length of 8.5 mm.

A tube (made of polyamide) having a tensile elastic modulus of 1,300 MPa (test method: ISO 527), a yielding strength of 40 MPa (test method: ISO527), an outer diameter of 1.2 mm, an inner diameter of 1.0 mm, a length of about 305 mm was used as the tube constituting the inner cylinder shaft 4. The end portion on the proximal end side of the tube was widened, and attached to the distal end portion of the small diameter portion of the push-in member 6 with an adhesive. Further, the distal end of the tube was widened, and a stainless steel pipe (outer diameter: 1.16 mm, inner diameter: 1.0 mm, length: 7 mm) was fitted into the lumen of the tube, and fixed with an adhesive, to be used as the inner cylinder shaft 4.

As the tube 5, a tube (made of polyimide) having a flexural modulus of 3.5 GPa (test method: ASTM D790), a Rockwell hardness of R 126 (test method: ASTM D785), an inner diameter of 1.25 mm, an outer diameter of 1.37 mm and a length of 295 mm was used. The tube 5 was inserted over the tube constituting the inner cylinder shaft 4 such that the end portion on the proximal end side of the tube 5 was in contact with the distal end of the small diameter portion of the pipe of the push-in member 6, before adhering the stainless steel pipe attached to the distal end of the inner cylinder shaft 4. Only the portion of about 2 mm, of the end portion on the proximal end side of the tube 5, was fixed to the inner cylinder shaft 4 with an adhesive.

The inner cylinder shaft assembly composed of the inner cylinder shaft 4, tube 5 and the push-in member 6 was inserted into the outer cylinder shaft assembly, and the cap for the holding member 3 was fitted to the holding member 3. Thereafter, the O-ring as the sealing member 8 was tightened such that the tightening force (having the same meaning as the sliding force between the inner cylinder shaft assembly and the outer cylinder shaft assembly) when the O-ring passes the intermediate portion and runs on the large diameter portion of the push-in member 6, was 15N. The O-ring was adjusted to be positioned at the end portion on the proximal end side of the intermediate portion of the push-in member 6, and this state was defined as a state where the balloon of the balloon catheter 100 is at its equilibrium length.

In the balloon catheter 100, the balloon 9 is configured to have a three-layer structure. As an inner layer balloon, a tube made of a natural rubber latex, and having an inner diameter of 4.5 mm and a thickness on one side of 0.3 mm, was attached onto the small diameter portion of the stepped pipe of the outer cylinder shaft 1 and onto the stainless steel pipe of the inner cylinder shaft 4, by winding a No. 0.2 Nylon string therearound and then fixing with an adhesive. Further, a tube made of a natural rubber latex, and having an inner diameter of 4.5 mm and a thickness on one side of 0.3 mm, was adhered with a rubber cement to a mesh weaved in the form of a cylinder using false twist yarns composed of a polyurethane and a polyester at a number of stitches of 50, to prepare an outer balloon assembly. The resulting outer balloon assembly was disposed on top of the inner layer balloon, and attached onto the small diameter portion of the stepped pipe of the outer cylinder shaft 1 and onto the stainless steel pipe of the inner cylinder shaft 4, by winding a No. 0.6 Nylon string therearound and then fixing with an adhesive, as an outer balloon.

In this manner, the balloon 9 having a three-layer structure, and having an inner layer made of a natural rubber latex, an intermediate layer made of a mesh, and an outer layer made of a natural rubber latex was obtained. The balloon was configured to have an equilibrium length of 25 mm, and a balloon diameter upon inflation of 26 mm.

Comparative Example 1

The same procedure as in Example 1 was repeated, except that the tube (made of polyimide) used in Example 1 was not attached during the preparation of the inner cylinder shaft 4, to produce a balloon catheter of Comparative Example 1. The inner cylinder shaft 4 of Comparative Example 1 had an outer diameter of 1.35 mm and an inner diameter of 0.94 mm.

Comparative Example 2

The same procedure as in Example 1 was repeated, except that a tube having an outer diameter of 1.1 mm and an inner diameter of 1.0 mm was used as the tube constituting the inner cylinder shaft 4, to produce a balloon catheter of Comparative Example 2.

Comparative Example 3

The same procedure as in Example 1 was repeated, except that a tube (made of a polyether block amide copolymer) having a tensile elastic modulus of 414 MPa (test method: ISO 527), a yielding strength of 23 MPa (test method: ISO 527), an outer diameter of 1.2 mm and an inner diameter of 1.0 mm was used as the tube constituting the inner cylinder shaft 4, to produce a balloon catheter of Comparative Example 3.

Comparative Example 4

The same procedure as in Example 1 was repeated, except that a tube was prepared by layering: a tube A (made of polyimide) having a flexural modulus of 3.5 GPa (test method: ASTM D790), a Rockwell hardness of R 126 (test method: ASTM D785), an inner diameter of 1.2 mm and a thickness of 0.06 mm; a tube B made of polyimide, and having an inner diameter of 1.35 mm and a thickness of 0.06 mm; and a tube C made of polyimide, and having an inner diameter of 1.5 mm and a thickness of 0.04 mm; and then adjusting to a length of about 310 mm, to be used as the tube 5, and the tube 5 was used instead of the inner cylinder shaft 4 and the stainless steel pipe attached to the distal end of the inner cylinder shaft 4, and that the end portion on the proximal end side of the tube 5 was adhered and fixed to the distal end of the small diameter portion of the push-in member 6, and the balloon 9 was attached to the tube 5, to produce a balloon catheter of Comparative Example 4.

Comparison of Example and Comparative Examples using Simulated Blood Vessel

Using a pressure-resistant hose having an outer diameter of 16 mm, an inner diameter of 10 mm and a length of 70 cm was used, one round of loop was prepared such that the center of the loop was formed at a position of about 16 cm from the end portion of the pressure-resistant hose, and such that the pressure-resistant hose was not flattened. The resultant was used as a simulated blood vessel. The curvature of the thus prepared loop had a diameter of 5 cm, when the central axis in a cross section of the pressure-resistant hose was taken as the circumference of the loop. The end portion of the pressure-resistant hose on the side at which the loop was formed constitutes the distal end side of the simulated blood vessel.

An introducer sheath (medical device approval number: 16100 BZZ00178000; manufactured by Togo Medikit Co., Ltd.) having a nominal diameter of 11 Fr. (measured inner diameter: 3.75 mm) was set to the end portion on the proximal end side of the pressure-resistant hose, and a 0.035-inch guide wire (medical device approval number: 22400BZX00511000; manufactured by Cook Medical Ltd.) having a length of 260 cm was placed to penetrate through the interior of the simulated blood vessel and the introducer sheath.

Each of the balloon catheters of Example 1 and Comparative Examples 1 to 4 was inserted into the interior of the simulated blood vessel from the proximal end side, along the guide wire, and the following tests (1) to (5) were carried out sequentially in this order, as the simulated tests in which the techniques of an operator for operating a balloon catheter within a blood vessel were simulated: (1) insertability into the 11 Fr. introducer sheath; (2) measurement of trackability to the loop portion of the simulated blood vessel; (3) the volume of water injected during balloon inflation until outer diameter of 26 mm is reached; (4) measurement of balloon deflation time from the fully inflated state; and (5) resistance force upon removal from the 11 Fr. introducer sheath (catheter withdrawability). The tests (1) to (5) were carried out sequentially in this order, and those evaluated as "x" in any of the tests were considered to be incapable of proceeding to the next procedure during the operation, and thus evaluated as "not performable".

The results of the tests (1) to (5) carried out sequentially in this order are shown in Table 1.

TABLE 1

| | Results of tests (1) to (5) carried out sequentially | | | | |
|---|---|---|---|---|---|
| | (1) Measurement of insertability into 11 Fr. introducer sheath | (2) Measurement of trackability to loop portion of simulated blood vessel | (3) Measurement of volume of water injected during balloon inflation until outer diameter of 26 mm is reached | (4) Measurement of balloon deflation time from fully inflated state | (5) Measurement of resistance force upon removal from 11 Fr. introducer sheath |
| Example 1 | ○ | ○ | 17.9 mL | 3.8 sec | ○ (14 N) |
| Comparative Example 1 | x | Not performable | Not performable | Not performable | Not performable |

TABLE 1-continued

Results of tests (1) to (5) carried out sequentially

| | (1) Measurement of insertability into 11 Fr. introducer sheath | (2) Measurement of trackability to loop portion of simulated blood vessel | (3) Measurement of volume of water injected during balloon inflation until outer diameter of 26 mm is reached | (4) Measurement of balloon deflation time from fully inflated state | (5) Measurement of resistance force upon removal from 11 Fr. introducer sheath |
|---|---|---|---|---|---|
| Comparative Example 2 | o | o | 20.1 mL | 4.5 sec | x |
| Comparative Example 3 | o | o | 20.7 mL | 4.8 sec | x |
| Comparative Example 4 | o | x | Not performable | Not performable | Not performable |

Further, separately from the simulated tests in which the techniques of an operator for operating a balloon catheter within a blood vessel were simulated, the results of any of the tests (1) to (5) when the tests were carried out individually, not sequentially in order, are shown in Table 2.

TABLE 2

Results of tests (1) to (5) carried out individually

| | (1) Measurement of insertability into 11 Fr. introducer sheath | (2) Measurement of trackability to loop portion of simulated blood vessel | (3) Measurement of volume of water injected during balloon inflation until outer diameter of 26 mm is reached | (4) Measurement of balloon deflation time from fully inflated state | (5) Measurement of resistance force upon removal from 11 Fr. introducer sheath |
|---|---|---|---|---|---|
| Comparative Example 1 | | o | 17.8 mL | 3.8 sec | |
| Comparative Example 4 | | | 17.7 mL | 4.8 sec | o (25 N) |

(1) Measurement of Insertability into 11 Fr. Introducer Sheath:

This measurement is a simulated reproduction of the operation of inserting a balloon catheter into a blood vessel. Each of the balloon catheters of Example 1 and Comparative Examples 1 to 4 was inserted into the 11 Fr. introducer sheath, and the insertability thereof was evaluated. When the operator was able to insert the balloon catheter into the 11 Fr. introducer sheath without problems, the balloon catheter was evaluated as insertable (o). When the operator was unable to insert the balloon catheter into the 11 Fr. introducer sheath by hand, or when some kind of damage occurred in the balloon catheter even if it could be inserted, the balloon catheter was evaluated as not insertable (x).

In the balloon catheter of Comparative Example 1, buckling occurred in the inner cylinder shaft 4 when the inner cylinder shaft assembly was slid and pushed 60 mm into the outer cylinder shaft assembly to stretch the balloon 9 and, thus, the balloon catheter was evaluated as not insertable (x) into the 11 Fr. introducer sheath. In contrast, the balloon catheters of Example 1 and Comparative Examples 2 to 4 were all evaluated as insertable (o) into the introducer sheath.

The length of the balloon when the inner cylinder shaft assembly was slid and pushed 60 mm into the outer cylinder shaft assembly to stretch the balloon 9 was 70 mm in each of the balloon catheters of Example 1 and Comparative Examples 2 to 4, and 56 mm in the balloon catheter of Comparative Example 1 in which buckling occurred.

(2) Measurement of Trackability to Loop Portion of Simulated Blood Vessel:

This measurement is a simulated reproduction of the operation of delivering the balloon catheter to an affected area, and carried out to investigate whether the balloon catheter can be delivered conforming to the curvature of the blood vessel. For each of the balloon catheters of Example 1, Comparative Example 2, Comparative Example 3 and Comparative Example 4, which had been evaluated as acceptable in the measurement of insertability into the 11 Fr. introducer sheath, the evaluation was carried out to investigate whether the balloon catheter can be delivered conforming to the guide wire, at the loop portion of the simulated blood vessel (the curvature of the loop had a diameter of 5 cm, when the central axis in a cross section of the pressure-resistant hose was taken as the circumference of the loop). When the balloon catheter was able to be inserted into the loop portion of the simulated blood vessel without problems, the balloon catheter was evaluated to have a good trackability (o). When the balloon catheter was unable to conform to the guide wire when being inserted into the loop portion of the simulated blood vessel to cause the deformation of the guide wire, or to cause the delamination of the coating of the guide wire, the balloon catheter was evaluated to have a poor trackability (x).

In the balloon catheter of Comparative Example 4, the resistance force when being inserted into the loop portion of the simulated blood vessel was extremely high, resulting in the occurrence of coating delamination of the guide wire.

Further, since the balloon catheter of Comparative Example 1 could not be inserted into the 11 Fr. introducer sheath, it was unable to carry out the tests (1) to (5) sequentially. However, when the measurement of trackability to the loop portion of the simulated blood vessel was carried out individually, the balloon catheter of Comparative Example 1 had a good trackability to the loop portion of the simulated blood vessel.

(3) Measurement of Volume of Water Injected during Balloon Inflation until Outer Diameter of 26 mm is Reached:

This measurement is a simulated reproduction of the operation of inflating the balloon at a narrow segment of a blood vessel. In each of the balloon catheters of Example 1, Comparative Example 2 and Comparative Example 3, water was injected into the interior of the catheter to inflate the balloon to measure the volume of water injected until the diameter of the balloon reached 26 mm. When a large volume of water is injected into the balloon, the length of the balloon in the longitudinal direction of the catheter is elongated, and this means that unnecessary stretching is occurring in the inner cylinder shaft of the balloon catheter. That is, avoiding the stretching of the inner cylinder shaft leads to reducing the probability of the occurrence of damage in the catheter, and thus, the volume of water injected into the balloon in this measurement is the smaller, the more preferred.

As a result of the measurement of the volume of water injected during balloon inflation until an outer diameter of 26 mm is reached, the volume of water injected was 20.1 mL in the balloon catheter of Comparative Example 1, and 20.7 mL in the balloon catheter of Comparative Example 3. In contrast, the volume of water injected in the balloon catheter of Example 1 was 17.9 mL, showing the lowest balloon volume.

Although it was unable to carry out the tests (1) to (5) sequentially for the balloon catheters of the Comparative Example 1 and Comparative Example 4, when the measurement of the volume of water injected during balloon inflation until an outer diameter of 26 mm is reached was carried out individually, the volume of water injected was 17.8 mL in the balloon catheter of Comparative Example 1, and 17.7 mL in the balloon catheter of Comparative Example 4, both of which were almost equal to the volume of water injected in the balloon catheter of Example 1.

(4) Measurement of Balloon Deflation Time from Fully Inflated State:

This measurement is a simulated reproduction of the operation of deflating the balloon after inflating the narrow segment of a blood vessel with the balloon. In each of the balloon catheters of Example 1, Comparative Example 2 and Comparative Example 3, a state in which the balloon was inflated to an outer diameter of 26 mm was defined as the fully inflated state, and the time point at this state was taken as the starting point of the measurement. From this state, water was sucked out by fully pulling the plunger of a 30 mL-syringe connected to the balloon catheter to deflate the balloon, and the time point at which the balloon was fully deflated was taken as the end point. Thus, the period of time from the starting point to the end point was measured. The period of time from the starting point to the end point refers, for example, in the catheter operation for expanding heart valves, to the period of time during which the balloon is inflated to block the blood flow. The shorter the period of this time, the less the burden on the patient.

As a result of the measurement of the balloon deflation time from the fully inflated state, the deflation time in the balloon catheter of Example 1 was 3.8 seconds, the deflation time in the balloon catheter of Comparative Example 2 was 4.5 seconds, and the deflation time in the balloon catheter of Comparative Example 3 was 4.8 seconds, revealing that the balloon catheter of Example 1 showed the shortest balloon deflation time.

Although it was unable to carry out the tests (1) to (5) sequentially for the balloon catheters of Comparative Example 1 and Comparative Example 4, when the measurement of the balloon deflation time from the fully inflated state was carried out individually, the deflation time in the balloon catheter of Comparative Example 1 was 3.8 seconds, and the deflation time in the balloon catheter of Comparative Example 4 was 4.8 seconds.

(5) Measurement of Resistance Force (Catheter Withdrawability) upon Removal from 11 Fr. Introducer Sheath:

This measurement is a simulated reproduction of the operation of removing the balloon catheter out of the body of the patient, after deflation of the balloon. A force gauge (manufactured by Imada Co., Ltd.) was attached to each of the balloon catheters of Example 1, Comparative Example 2 and Comparative Example 3, and the operation of removing the catheter from the 11 Fr. introducer sheath was carried out to measure the resistance force generated between the 11 Fr. introducer sheath and the balloon catheter. Specifically, the inner cylinder shaft assembly was slid and pushed 60 mm into the outer cylinder shaft assembly to stretch the balloon 9, in each of the balloon catheters, and the resistance force upon removal of the balloon catheter from the 11 Fr. introducer sheath was measured. In addition, when the operator was able to remove the balloon catheter without causing damage thereto, the balloon catheter was evaluated to have a good catheter withdrawability (○). When the operator was unable to remove the balloon catheter from the 11 Fr. introducer sheath, or when some kind of damage occurred in the balloon catheter even if it could be removed, the balloon catheter was evaluated to have a poor catheter withdrawability (x).

As a result, the resistance force upon removal of the balloon catheter of Example 1 was 14 N, and it was possible to remove the balloon catheter from the 11 Fr. introducer sheath without causing damage to the balloon catheter. Therefore, the balloon catheter of Example 1 was evaluated to have a good catheter withdrawability (○). In the balloon catheters of Comparative Example 2 and Comparative Example 3, the resistance force upon removal was 14 N, which was equal to the resistance force in Example 1. However, in each of the balloon catheters of Comparative Example 2 and Comparative Example 3, a local permanent strain was generated in the inner cylinder shaft 4 upon removal from the 11 Fr. introducer sheath to cause the narrowing of the lumen. This led to the deterioration of the slidability with the guide wire, as a result of which the balloon catheter got stuck with the guide wire.

When the balloon catheter gets stuck with the guide wire, the balloon catheter moves together with the guide wire. Originally, the guide wire must serve as a guide rail for the catheter, in a catheter operation. If the catheter moves together with the guide wire, there is a possibility that the blood vessel or tissue may be damaged during the operation.

Although it was unable to carry out the tests (1) to (5) sequentially for the balloon catheters of the Comparative Example 1 and Comparative Example 4, when the measurement of resistance force upon removal from the 11 Fr. introducer sheath was carried out individually, the balloon catheter of Comparative Example 4 could be removed from the 11 Fr. introducer sheath without causing damage to the balloon catheter, and thus could be evaluated as having a good catheter withdrawability (○). However, the measured resistance force was 25 N, which was about twice as high as compared to the balloon catheter of Example 1.

INDUSTRIAL APPLICABILITY

My balloon catheters can be used, for example, in endovascular treatments such as the treatment of valvular stenosis and the treatment of atrial fibrillation.

The invention claimed is:

1. A balloon catheter, comprising:
   a flexible outer cylinder shaft;
   a holding member for an operator to hold during operation, said holding member connected to a proximal end portion of said flexible outer cylinder shaft;
   a sealing member that maintains liquid tightness incorporated in said holding member;
   a flexible inner cylinder shaft;
   a tube having a Rockwell hardness of R 115 or more, a flexural modulus of 3.0 to 4.5 GPa, and a thickness of 0.06 to 0.12 mm;
   a push-in member connected to a proximal end portion of said flexible inner cylinder shaft;
   a pull-out prevention member connected to said push-in member; and
   a balloon composed of an elastic material and connected to each of a distal end portion of said flexible outer cylinder shaft and a distal end portion of said flexible inner cylinder shaft;
   wherein said tube is fitted over said flexible inner cylinder shaft over an area from a connection portion between the push-in member and said flexible inner cylinder shaft and excluding a connecting portion between said balloon and said flexible inner cylinder shaft, and
   said tube is only fixed to said flexible inner cylinder shaft at only either a distal end portion of the tube or a proximal end portion of the tube such that application of a tensile force applied by the push-in member to the flexible inner cylinder shaft causes an unfixed portion of the flexible inner cylinder shaft to slide relative to the tube.

2. The balloon catheter according to claim 1, wherein a clearance between an inner diameter of said tube and an outer diameter of said flexible inner cylinder shaft is 0.01 to 0.1 mm.

3. The balloon catheter according to claim 1, wherein said flexible inner cylinder shaft has a tensile elastic modulus of 500 to 1,400 MPa, a thickness of 0.1 to 0.23 mm and a yielding strength of 25 MPa or more.

4. The balloon catheter according to claim 1,
   wherein said push-in member has a pipe with a varying outer diameter;
   wherein a transition portion where said the varying outer diameter of said push-in member has a tapered shape, and respective outer diameters of said pipe are configured to decrease in a direction from a proximal end side toward a distal end side of the pipe; and
   said pull-out prevention member is provided on the pipe of said push-in member at a position where a first change in the outer diameter occurs in a direction toward the distal end side, in a state where said balloon is at an equilibrium length.

5. A balloon catheter for ablation, comprising:
   the balloon catheter according to claim 1;
   an electrode lead wire capable of conducting a high frequency current and provided in a space between said inner cylinder shaft and said outer cylinder shaft and;
   a temperature sensor lead wire that is configured to transmit temperatures in said balloon to an outside of the balloon, said temperature sensor lead wire being provided in the space between said flexible inner cylinder shaft and said flexible outer cylinder shaft; and
   a lead wire cladding tube through which said electrode lead wire and said temperature sensor lead wire are inserted so that said electrode lead wire and said temperature sensor lead wire are led into the space between said inner cylinder shaft and said outer cylinder shaft, from the outside of the balloon;
   wherein said electrode lead wire and said temperature sensor lead wire are made of metals different from each other, and contact each other in an interior of said balloon; and
   said lead wire cladding tube is in the form of a pipe including a portion with a varying outer diameter, and is provided on a distal side from a handle portion of said push-in member to be slidable while maintaining liquid tightness via said sealing member.

* * * * *